(12) United States Patent
Charron et al.

(10) Patent No.: US 11,207,456 B2
(45) Date of Patent: Dec. 28, 2021

(54) METHOD AND DEVICE FOR INFUSION OF PHARMACOLOGIC AGENTS AND THROMBUS ASPIRATION IN ARTERY (71) Applicant: VALORISATION RECHERCHE HSCM, LIMITED PARTNERSHIP, Montreal (CA)

(72) Inventors: Thierry Charron, Mont St-Hilaire (CA); Domenic Santoianni, Kirkland (CA); Marwan Abboud, Pierrefonds (CA); Guy Rousseau, Ile Bizard (CA); Aime-Robert Leblanc, Montreal (CA)

(73) Assignee: VALORISATION RECHERCHE HSCM, LIMITED PARTNERSHIP, Montreal (CA)

( * ) Notice: Subject to any disclaimer, the term of this patent is extended or adjusted under 35 U.S.C. 154(b) by 211 days.

(21) Appl. No.: 15/824,235

(22) Filed: Nov. 28, 2017

(65) Prior Publication Data

US 2018/0078685 A1    Mar. 22, 2018

Related U.S. Application Data

(62) Division of application No. 14/414,315, filed as application No. PCT/CA2013/050534 on Jul. 10, 2013, now Pat. No. 9,855,375.

(Continued)

(51) Int. Cl.
*A61M 1/00*    (2006.01)
*A61M 25/10*    (2013.01)
(Continued)

(52) U.S. Cl.
CPC .............. *A61M 1/85* (2021.05); *A61B 17/22* (2013.01); *A61M 25/09* (2013.01); *A61M 25/10* (2013.01);
(Continued)

(58) Field of Classification Search
CPC ........ A61M 1/0084; A61M 2025/0031; A61M 2025/1052; A61M 2025/1079;
(Continued)

(56) References Cited

U.S. PATENT DOCUMENTS 3,929,126 A     12/1975 Corsaut
4,445,892 A *    5/1984 Hussein ............. A61B 1/00082
                                                              600/108
(Continued)

FOREIGN PATENT DOCUMENTS

EP     1467794 A2    10/2004
EP     1926453 A1     6/2008
(Continued)

*Primary Examiner* — Quynh-Nhu H. Vu
(74) *Attorney, Agent, or Firm* — Norton Rose Fulbright Canada LLP (57) ABSTRACT

A catheter device and method for treating an artery with thrombus, the catheter comprising an inflatable member. A carrier catheter has a proximal end and a distal end adapted to be inserted percutaneously into an artery, the carrier catheter having a tubular body adjacent to a rear end of the inflatable member. An inflating tube passes through the tubular body and having an open front end in fluid communication with the inflatable member to inflate same. An infusion tube is adapted to infuse pharmacologic agents, the infusion tube passing through the tubular body and having an open front end extending beyond the inflatable member. An aspiration tube is adapted to aspire the thrombus, the aspiration tube passing through the tubular body and having an open front end between the carrier catheter and the inflatable member.

11 Claims, 5 Drawing Sheets

Related U.S. Application Data (60) Provisional application No. 61/669,934, filed on Jul. 10, 2012.

(51) Int. Cl.
    *A61M 25/09* (2006.01)
    *A61B 17/22* (2006.01)
    *A61M 25/00* (2006.01)

(52) U.S. Cl.
    CPC .............. *A61B 2017/22051* (2013.01); *A61B 2017/22079* (2013.01); *A61B 2017/22084* (2013.01); *A61M 2025/0031* (2013.01); *A61M 2025/1052* (2013.01); *A61M 2025/1079* (2013.01); *A61M 2210/12* (2013.01)

(58) Field of Classification Search
    CPC .. A61M 2210/12; A61M 25/09; A61M 25/10; A61B 17/22; A61B 2017/22051; A61B 2017/22079; A61B 2017/22084
    See application file for complete search history.

(56) References Cited

U.S. PATENT DOCUMENTS

| | | | |
|---|---|---|---|
| 5,060,201 A | 7/1991 | Palestrant | |
| 5,143,062 A | 9/1992 | Peckham | |
| 5,311,864 A * | 5/1994 | Huerta | A61M 16/04 128/207.15 |
| 5,370,609 A * | 12/1994 | Drasler | A61B 17/32037 604/22 |
| 5,728,123 A | 3/1998 | Lemelson | |
| 5,911,725 A | 6/1999 | Boury | |
| 5,941,869 A | 8/1999 | Patterson et al. | |
| 6,176,844 B1 | 1/2001 | Lee | |
| 6,454,757 B1 | 9/2002 | Nita | |
| 6,520,975 B2 | 2/2003 | Branco | |
| 7,399,307 B2 * | 7/2008 | Evans | A61B 17/22 606/159 |
| 7,654,264 B2 * | 2/2010 | Clayton | A61M 16/0479 128/207.15 |
| 7,686,781 B2 | 3/2010 | Vinten-Johansen | |
| 2001/0049548 A1 * | 12/2001 | Vardi | A61F 2/954 623/1.11 |
| 2002/0044907 A1 * | 4/2002 | Constantz | A61M 25/1011 423/481 |
| 2002/0058904 A1 * | 5/2002 | Boock | A61B 17/221 604/35 |
| 2002/0091407 A1 * | 7/2002 | Zadno-Azizi | A61M 25/0054 606/200 |
| 2003/0073953 A1 * | 4/2003 | Mische | A61B 17/22012 604/152 |
| 2004/0049225 A1 | 3/2004 | Denison | |
| 2004/0138614 A1 | 7/2004 | Hahnen | |
| 2004/0158270 A1 | 8/2004 | Wyzgala et al. | |
| 2004/0162548 A1 * | 8/2004 | Reiser | A61B 18/24 606/7 |
| 2004/0220515 A1 * | 11/2004 | Constantz | A61M 25/10 604/43 |
| 2006/0004286 A1 | 1/2006 | Chang | |
| 2007/0083187 A1 | 4/2007 | Eversull | |
| 2009/0171301 A1 * | 7/2009 | Becker | A61M 3/0283 604/264 |
| 2009/0318798 A1 | 12/2009 | Singh | |
| 2011/0015564 A1 * | 1/2011 | Bonnette | A61B 17/32037 604/22 |
| 2011/0046542 A1 * | 2/2011 | Evans | A61B 17/320758 604/22 |
| 2012/0083868 A1 * | 4/2012 | Shrivastava | A61B 17/221 623/1.11 |
| 2012/0143054 A1 | 6/2012 | Eaton | |
| 2012/0259215 A1 * | 10/2012 | Gerrans | A61M 25/1011 600/435 |
| 2013/0013007 A1 | 6/2013 | Broome | |
| 2014/0214003 A1 | 7/2014 | Yang | |

FOREIGN PATENT DOCUMENTS

| | | |
|---|---|---|
| WO | 03059179 A1 | 7/2003 |
| WO | 03/097122 A2 | 11/2003 |

* cited by examiner

METHOD AND DEVICE FOR INFUSION OF PHARMACOLOGIC AGENTS AND THROMBUS ASPIRATION IN ARTERY

CROSS-REFERENCE TO RELATED APPLICATION

The present application is a divisional application of U.S. application Ser. No. 14/414,315 filed on Jan. 12, 2015 which is a National Stage Entry of PCT/CA2013/050534 filed on Jul. 10, 2013 which claims priority on U.S. Provisional Application No. 61/669,934, filed on Jul. 10, 2012, and incorporated herein by reference.

FIELD OF THE DISCLOSURE

The present application pertains to a method and device for the infusion of pharmacologic agents and thrombus aspiration in atherosclerotic vascular disease.

BACKGROUND OF THE ART

Atherosclerotic vascular disease is one of the main causes of adult mortality in developed countries. The sudden occlusion of a coronary artery subsequent to a plaque rupture remains one of the most frequent causes of myocardial infarction.

Percutaneous coronary intervention, when performed promptly, is an efficient reperfusion method. However, there remains issues with the opening of coronary arteries. Despite efficient and prompt intervention, some patients will present a condition known as no-reflow in which, in spite of the fact that the coronary artery is opened without residual stenosis, myocardial perfusion is diminished. No-reflow may be caused by two distinct phenomenons. A first one is the distal embolization of microparticles in blood vessels. A second phenomenon is reperfusion injury.

It has been shown that aspiration catheters are efficient in removing blood clots from arteries in the myocardial infarction status and thus improve the blood flow in the infarction zone. However, despite their efficiency, such catheters do not necessarily prevent the distal embolization of microparticles subsequent to their use. Also, such catheters do not allow drug infusion distally to the occlusion prior to thrombus aspiration.

SUMMARY OF THE APPLICATION

It is therefore an aim of the present disclosure to provide a novel method for infusing pharmacologic agents and/or performing thrombus aspiration in atherosclerotic vascular disease.

It is a further aim of the present disclosure to provide a novel device for infusing pharmacologic agents and/or performing thrombus aspiration in atherosclerotic vascular disease.

Therefore, in accordance with a first embodiment of the present application, there is provided a method for treating an artery having a thrombus comprising: percutaneously positioning a catheter with an infusion tube in the artery proximally to the thrombus; passing a tip of the infusion tube through the thrombus; and infusing at least one pharmacologic agent distally to the thrombus via the infusion tube.

Further in accordance with the first embodiment of the present application, positioning the catheter comprises positioning an inflatable member of the catheter proximally to the thrombus, and further comprising inflating the inflatable member proximally to the thrombus.

Still further in accordance with the first embodiment of the present application, inflating the inflatable member proximally to the thrombus is performed prior to infusing at least one pharmacologic agent distally to the thrombus.

Still further in accordance with the first embodiment of the present application, positioning the catheter further comprises positioning an aspiration tube of the catheter proximally to the thrombus, the aspiration tube being proximal to the inflatable member.

Still further in accordance with the first embodiment of the present application, there is performed an aspiration via the aspiration tube while deflating the inflatable member to aspire the thrombus.

Still further in accordance with the first embodiment of the present application, performing the aspiration is initiated before deflating the inflatable member.

Still further in accordance with the first embodiment of the present application, positioning the catheter and passing of the tip are done by moving the catheter over a guide wire.

Still further in accordance with the first embodiment of the present application, moving the catheter over the guide wire comprises moving the catheter and the infusion tube simultaneously.

Still further in accordance with the first embodiment of the present application, moving the catheter over the guide wire comprises moving the catheter and the infusion tube simultaneously by the infusion tube sliding on the guide wire.

In accordance with a second embodiment of the present disclosure, there is provided a catheter device for thrombus aspiration comprising: an inflatable member; a carrier catheter having a proximal end and a distal end adapted to be inserted percutaneously into an artery, the carrier catheter having a tubular body adjacent to a rear end of the inflatable member; an inflating tube passing through the tubular body and having an open front end in fluid communication with the inflatable member to inflate same; an infusion tube adapted to infuse pharmacologic agents, the infusion tube passing through the tubular body and having an open front end extending beyond the inflatable member; and an aspiration tube adapted to aspire the thrombus, the aspiration tube passing through the tubular body and having an open front end between the carrier catheter and the inflatable member.

Further in accordance with the second embodiment of the present application, at least one radio-opaque marker is at a distal end of the infusion tube.

Still further in accordance with the second embodiment of the present application, at least one radio-opaque marker is on at least one of a distal end and a proximal end of the inflatable member.

Still further in accordance with the second embodiment of the present application, said radio-opaque markers are at the distal end and the proximal end of the inflatable member.

Still further in accordance with the second embodiment of the present application, a guide wire is received in the infusion tube.

Still further in accordance with the second embodiment of the present application, a proximal end of the carrier catheter has a tapered profile.

Still further in accordance with the second embodiment of the present application, a proximal end of the aspiration tube is coterminous with a proximal end of the carrier catheter.

Still further in accordance with the second embodiment of the present application, the proximal end of the carrier catheter has a tapered profile.

Still further in accordance with the second embodiment of the present application, the carrier catheter, the inflating tube, the infusion tube and the aspiration tube are integrally connected to one another.

DESCRIPTION OF THE PREFERRED EMBODIMENTS

Figure 4:
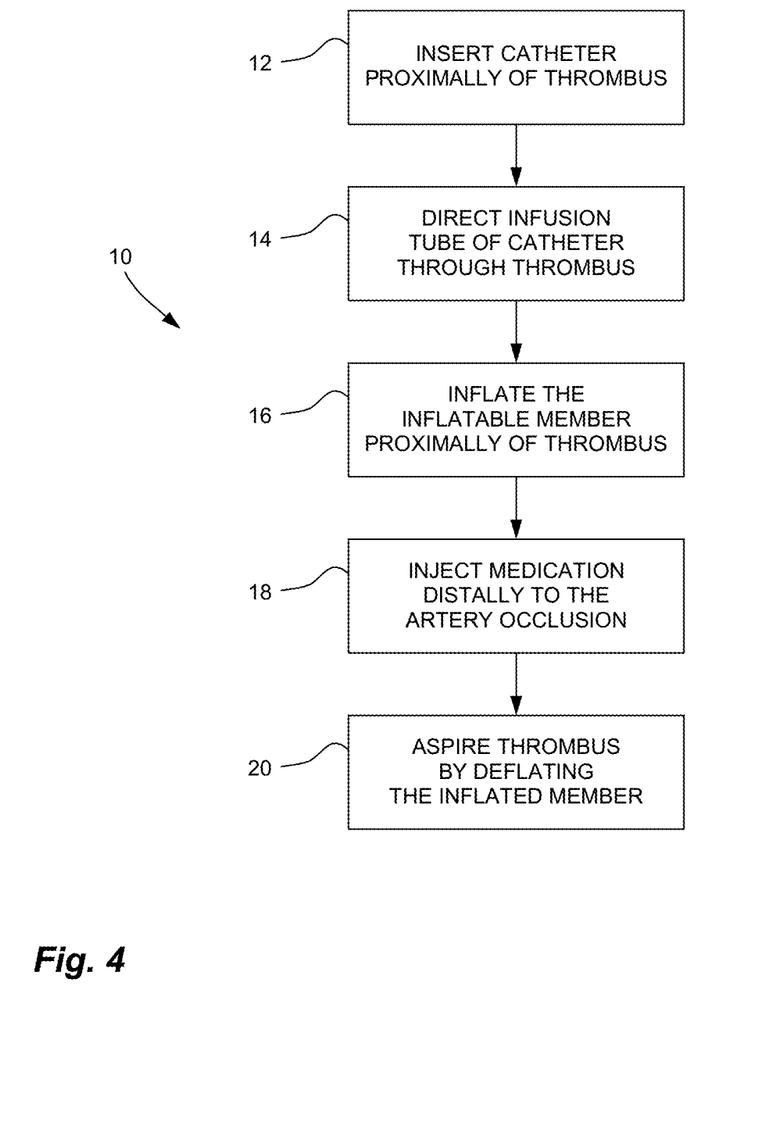
FIG. 4 is a flowchart of a method for infusing a pharmacologic agent and performing thrombus aspiration in accordance with another embodiment of the present disclosure

Referring to the drawings and, more particularly, to FIG. 4, there is shown at 10 a method for performing thrombus aspiration in accordance with an embodiment of the present disclosure. A catheter device that may be used to infuse pharmacologic agents and perform thrombus aspiration according to the method is described hereinafter.

According to 12, with the thrombus (a.k.a., blood clot, plaque rupture, artery occlusion) being localized, a catheter device is inserted into the coronary artery proximally of the artery occlusion, to be directed distally in the artery toward the thrombus.

According to 14, an infusion tube of the catheter device is directed through the blood clot. One way to perform this step is to firstly pass a guide wire through the blood clot. The infusion tube at the end of the catheter device is subsequently guided along the guide wire in an over-the-wire fashion through the occlusion. Therefore, the tip of the infusion tube of the catheter is distal of the blood clot after insertion.

The infusion tube may be localized by the presence of radio-opaque markers. Fluoroscopic imagery may be used to locate the infusion tube relative to the thrombus in the treated artery.

According to 16, an inflatable member on the catheter device is inflated proximally of the blood clot.

According to 18, a pharmacologic agent is infused into the infarction zone distally of the occlusion. As the artery is blocked by the occlusion and the inflated member, the pharmacologic agent will diffuse and be absorbed locally, distal to the blood clot.

The infusion of the pharmacologic agent may also be performed prior to the inflation of the inflatable member.

According to 20, the blood clot is vacuumed out of the artery so as to open the artery. The aspiration tube of the catheter device is proximally positioned relative to the inflatable member. Hence, the inflatable member must be deflated prior to the aspiration, for the aspiration to be performed on the blood clot.

In one embodiment, the aspiration is initiated while the inflatable member is inflated. This causes a relative negative pressure between the tip of the aspiration tube and the inflated member. When the inflatable member is deflated, a sudden pressure drop will be created at the thrombus, ensuring that most of the blood clot is captured and aspired out of the artery.

Subsequently, the various steps for terminating the intervention are performed, including the removal of the various units of the catheter device. It is pointed out that the method 10 may be performed according to any suitable sequence.

Figure 1:
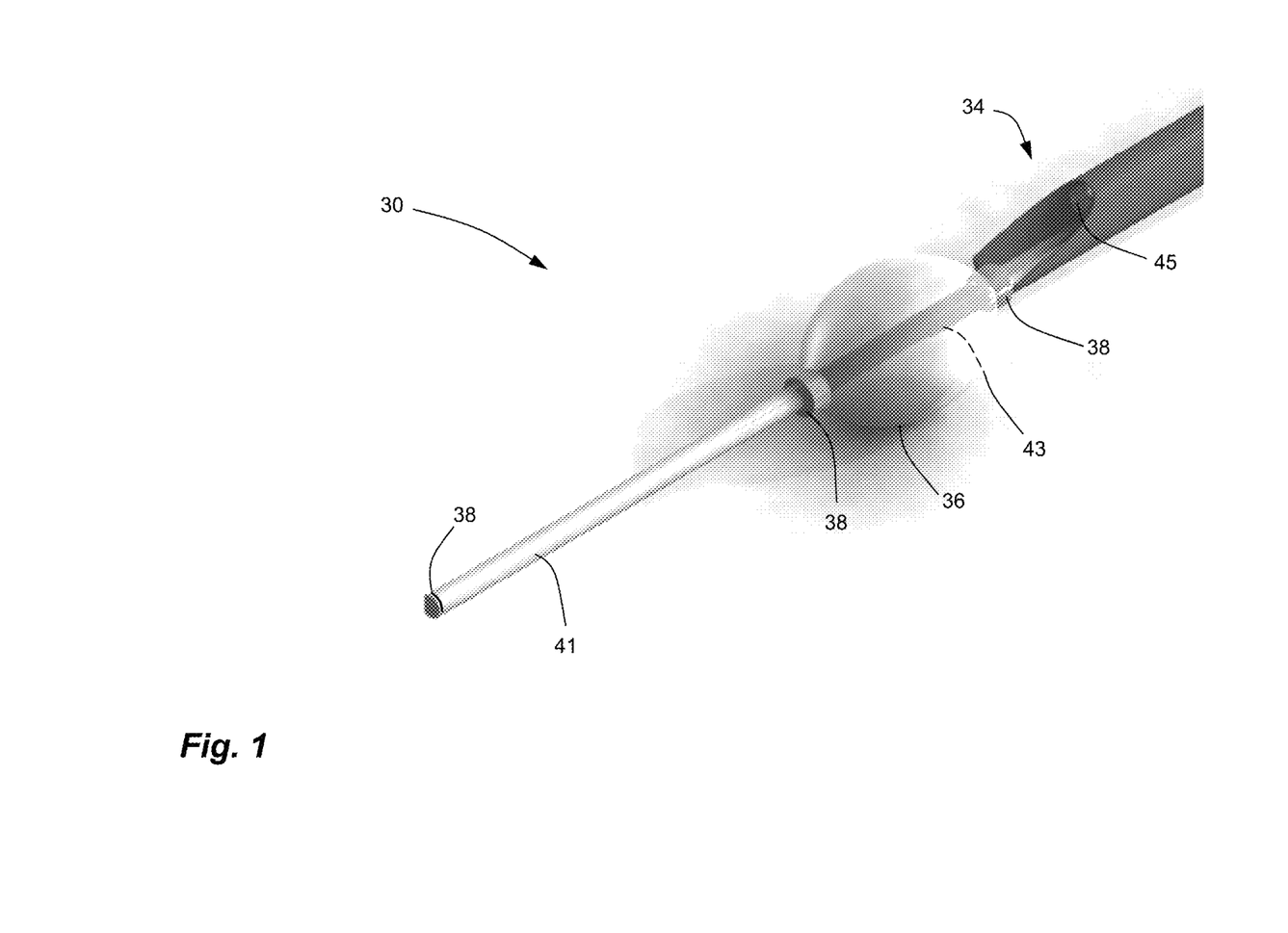
FIG. 1 is a perspective view of a catheter device for infusing a pharmacologic agent and for thrombus aspiration in accordance with an embodiment of the present disclosure.
Figure 2:
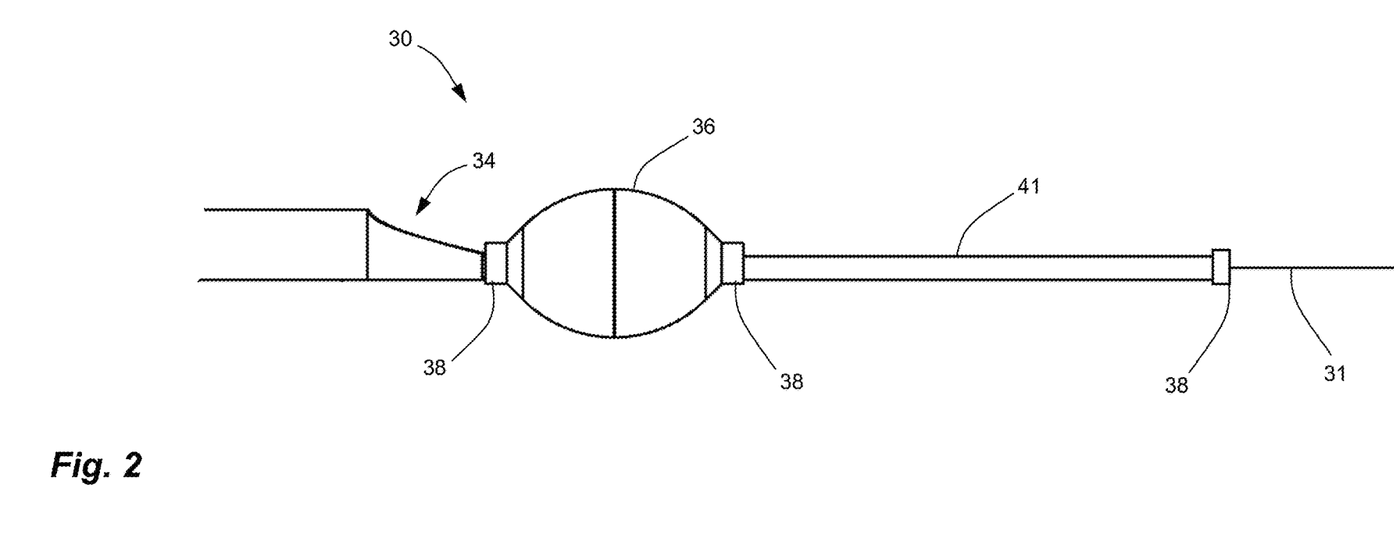
FIG. 2 is a schematic side view of the catheter device of FIG. 1.
Figure 3:
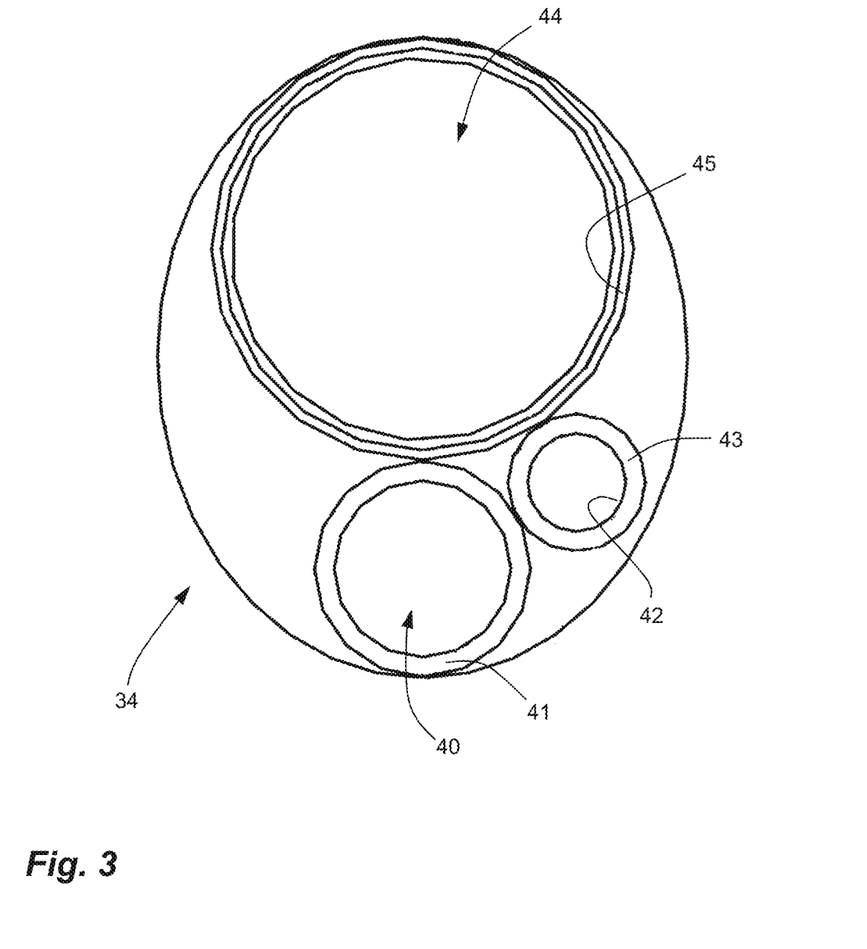
FIG. 3 is a sectional view of a carrier catheter of the catheter device of FIG. 1.

Referring to FIGS. 1 to 3, a catheter device in accordance with the present disclosure is generally shown at 30. The catheter device 30 may be used for the infusion of pharmacologic agents and for thrombus aspiration in accordance with the methodology described for method 10 of FIG. 4, and method 50 of FIG. 5 as described hereinafter.

The catheter device 30 is introduced over a guide wire 31 (FIG. 2) that is inserted into the coronary artery. The catheter device has a hydrophilic surface, so as to slide within the artery with reduced invasiveness.

The catheter device 30 is then slid along the guide wire 31. A carrier catheter 34, also known as an outer jacket of the catheter device 30, has an hydrophilic surface. According to an embodiment, the carrier catheter 34 is made of polyether block amide (e.g., Pebax™ 5533). As seen in FIG. 2, the front end of the aspiration tube of the carrier catheter 34 has a tapered profile to increase the aspiration area. An inflatable member 36 may be positioned at the front end of the carrier catheter 34. The inflatable member 36 may be any suitable type of inflatable material, such as a balloon. According to an embodiment, the inflatable member 36 is made of a substantially compliant membrane, so as to distribute inflating pressure uniformly on the inner surface of the artery.

Markers 38 of detectable material may be provided at one or both extremities of the inflatable member 36 for localization thereof, and at a tip of an infusion tube 41 (FIG. 2). For instance, radio-opaque material may be used for fluoroscopic localization, such as platinum with an iridium content (e.g., 10%). Alternatives are considered as well. According to an embodiment, the markers 38 have an inner diameter of 0.023", a wall of 0.001" and an outside diameter of 0.025".

Referring to FIG. 3, a section of the carrier catheter 34 is shown. The infusion tube 41 of the carrier catheter 34 has a passage 40 adapted to receive the guide wire 31, and to infuse medication. The infusion tube 41 itself is sized for the sliding displacement on the guide wire 31. The infusion tube 41 is subsequently used for infusion of pharmacologic agents, when the guide wire 31 is removed. The infusion tube 41 is open-ended at the front end of the carrier catheter 34, and its tip projects beyond the inflatable member 36. The infusion tube 41 may consist of any appropriate material. According to an embodiment, the infusion tube 41 may be made from a single extruded material. However, a combination of layers may be considered as well, such as high-density polyethylene (e.g., HDPE LR734, 25%) and/or polyether block amide (e.g., Pebax™ 7233, 75% of outer layer) and/or Plexar™ (e.g., middle layer of Plexar™ 3080). As an example, the infusion tube 41 may have an inner diameter of 0.018", a wall thickness of 0.0020" and an outer diameter of 0.022". Other dimensions are considered as well.

An inflating tube 43 is also part of the carrier catheter 34 and has a lumen 42 opening into the inflatable member 36 at the front end of the catheter device 30, for injection of a fluid into the inflatable member 36 by the inflating tube 43

(although the inflatable member 36 could be inflated with any other of the tubes). According to an embodiment, the inflating tube 43 may be made from a single extruded material. However, a combination of layers may be considered as well, such as high-density polyethylene (e.g., HDPE LR734, 25%) and/or polyether block amide (e.g., Pebax™ 7233, 75% of outer layer) and/or Plexar™ (e.g., middle layer of Plexar™ 3080). As an example, the inflating tube 43 may have an inner diameter of 0.018", a wall thickness of 0.0020" and an outer diameter of 0.022". Other dimensions are considered as well. Any appropriate type of fluid may be used. For instance, a mixture of saline and iodine contrast is commonly used for inflating balloons in percutaneous coronary intervention.

Still referring to FIG. 3, a passage 44 is also defined in the carrier catheter 34, and is part of an aspiration tube 45. The aspiration tube 45 is open-ended at the front end of the carrier catheter 34, and may be coterminous therewith in the manner shown in FIG. 1. The open end of the aspiration tube 45 is offset relative to the open end of the infusion tube 41, and is hence proximally located in the artery relative to a position of the inflatable member 36 and of the open end of the infusion tube 41. The aspiration tube 45 may be made from a combination of layers, such as polytetrafluoroethylene, a stainless steel braid (e.g., 0.0005" thickness for 0.005" width of flat wire with 44 pics/in), and a polyether block amide lumen (e.g., Pebax™ 6333). As an example, the aspiration tube 45 may have an inner diameter of 0.040", a wall thickness of 0.0025" and an outer diameter of 0.045". Other dimensions are considered as well. According to an embodiment, a polytetrafluoroethylene (PTFE) tube is placed over a mandrel also covered with PTFE, and the stainless steel braid is then positioned on the PTFE.

Markers may also be provided at the front end of the aspiration tube 45 to localize the front end of the tube 45 relative to the blood clot, using any appropriate imaging technique.

The tubes 41, 43 and 45 emerge out of the proximal end of the carrier catheter 34, with their open external ends being outside of the body, so as to be connected to appropriate means. The tubes 41, 43 and/or 45 may be equipped with suitable connectors (e.g., luers) for connection to the various devices (e.g., syringe). The infusion tube 41 is connected to a source of pharmacologic agents, such as a syringe, etc, for the controlled infusion of pharmacologic agents via the catheter device 30. As mentioned above, the inflating tube 43 is connected to a source of fluid for pressurization of the inflatable member 36.

The aspiration tube 45 is connected to an aspiration mechanism, such as a vacuuming syringe or the like. Accordingly, an aspiration action performed at the external end of the aspiration tube 45 causes an aspiration at the open internal end of the aspiration tube 45. As mentioned above, as the open internal end of the aspiration tube 45 is positioned adjacent to the blood clot in the thrombus aspiration application, the blood clot is vacuumed away from the artery via the aspiration tube 45.

Any appropriate material may be used for the tubes. According to other embodiments, the infusion tube 41 and the inflating tube 43 are, for instance, made of polyimide of medical grade, or any other relatively compliant material. One material that may be used for the aspiration tube 45 is braided reinforced polyimide, to ensure that the aspiration tube 45 maintains its structurally integrity despite the vacuuming pressure in the tube 45. During manufacturing, the outer jacket making up the carrier catheter 34 may be slid over the tubes 41, 43 and 45. With the tubes 41, 43 and 45 fixed and aligned with the outer jacket thereon, they may be passed through a heated die, with the outer jacket 34 fusing all together to give the shape of FIG. 3, or any other appropriate shape. Hence, these components are integrally connected to one another.

Contemplated dimensions are set forth below, by way of example, and for illustrative purposes. It is understood that the dimensions may be greater or smaller than those set forth below. The dimensions are in inches.

The carrier catheter 34 has an oval section of 0.065.times.0.054. The inner and outer diameters of the infusion tube 41 are 0.018 and 0.022; the inner and outer diameters of the inflating tube 43 are 0.010 and 0.014; the inner and outer diameters of the aspiration tube 45 are 0.039 and 0.043. The length of the inflatable member 36 is 0.200. All dimensions are given as an example, and it is contemplated to provide the above-referred components with a slight variation from these values.

Now that the catheter device 30 has been described, its use in a thrombus aspiration application is described, according to the method 10 of FIG. 4.

Referring concurrently to FIGS. 1 to 4, once the thrombus is localized, the guide wire is inserted into the coronary artery proximally of the artery occlusion, and is directed distally toward the thrombus, in accordance with 12. The front end of the guide wire 31 passes through the thrombus.

According to 14, the catheter device 30, mounted onto the guide wire 31 (with the guide wire being in the passage 40 of the infusion tube 41), is guided toward the blood clot by sliding engagement on the guide wire 31. The tip of the infusion tube 41 of the catheter device 30 is directed through the blood clot. Therefore, the open-ended tip of the infusion tube 41 is distally located relative to the blood clot, while the inflatable member 36 is proximally located relative to the blood clot. The guide wire 31 is then removed out of the artery.

The inflatable member 36 and/or the tip of the infusion tube 41 are localized in the artery, using the detectable markers 38. Fluoroscopic imagery or any other appropriate method may be used to locate the markers 38 relative to the thrombus in the treated artery.

According to 16, the inflatable member 36 is inflated proximally to the blood clot. This is performed by injecting fluid into the open external end of the inflating tube 43.

According to 18, the pharmacologic agent is infused in the infarction zone distally of the occlusion, by the infusion tube 41 in the infusion passage 40 now free of the guide wire (guide wire previously removed). As the artery is blocked by the occlusion, or the inflated balloon 36, the pharmacologic agent is absorbed locally.

The infusion of the pharmacologic agent may also be performed prior to inflating of the inflatable member 36.

According to 20, the blood clot is vacuumed out of the artery so as to open the artery. The aspiration tube 45 is adjacent to the blood clot, but separated therefrom by the inflated member 36. The aspiration tube 45 may be stiffened by a stylet for insertion of the carrier catheter 34 into the artery. The stylet is thus removed prior to the aspiration. An aspiration mechanism, such as a vacuuming syringe, is connected to the open external end of the aspiration tube 45 to perform the thrombus aspiration, but with the deflating of the inflated member 36 performed right after aspiration is initiated, to create a sudden pressure drop at the occlusion. Also, a back and forth motion of the catheter 30 will help to aspire the blood clot while the aspiration is performed.

The catheter device 30 may then be removed from the artery, and all necessary steps are performed to complete the angioplasty.

Numerous pharmacologic agents may be used for the infusion, the doses of which are selected on a case-by-case basis by appropriate personnel. Among the pharmacologic agents that can be used are: adenosine and adenosine receptor agonists, beta blockers, angiotensin-converting enzyme inhibitor, angiotensin-receptor blockers, aldosterone, calcium channel blockers (Verapamil, Diltiazem, Nifedipine), cyclosporin, calpain inhibitor, sodium-proton exchanger inhibitor, NO donor, cox-2 inhibitor, statins, TNF-alpha, endothelin receptor antagonists, antiplatelet, antithrombotic, erythropoietin, anti-leukocyte complement inhibitors, opioid, anesthetic, $K_{ATP}$ "openers", insulin, thrombin and fragments, melatonin, $H_2S$, bradykinin, cellular therapy, gene therapy, with the proper catheter.

Figure 5:
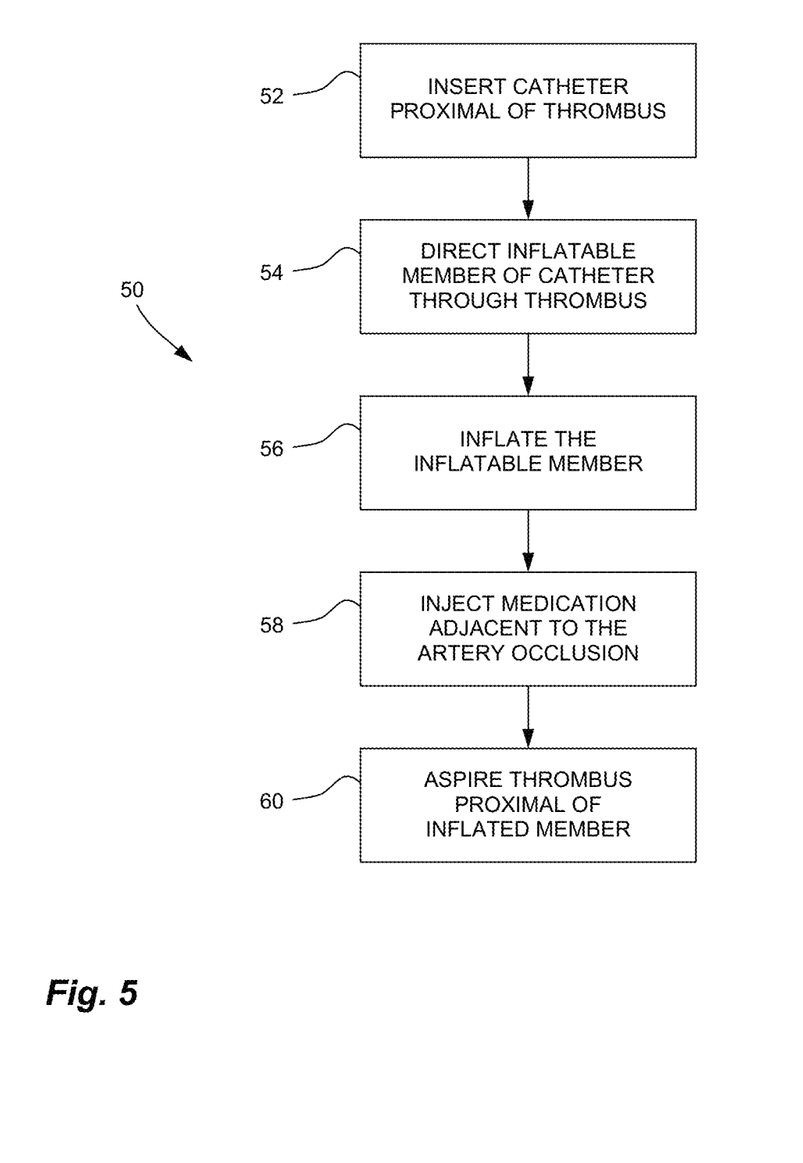
FIG. 5 is a flowchart of a method for infusing a pharmacologic agent and performing thrombus aspiration in accordance with yet another embodiment of the present disclosure.

Referring to the drawings and, more particularly, to FIG. 5, there is shown at 50 yet another method for infusing a pharmacologic agent and for performing thrombus aspiration in accordance with an embodiment of the present disclosure. The above-referred catheter device may be used to perform the infusion of medication and thrombus aspiration according to the method 50 described hereinafter.

According to 52, with the thrombus (a.k.a., blood clot, plaque rupture, artery occlusion) being localized, a catheter device is inserted into the coronary artery proximal to the artery occlusion, to be directed distal to the artery toward the thrombus.

According to 54, an inflatable member of the catheter device, such as a balloon, is directed through the blood clot. One way to perform this step is to firstly pass a guide wire through the blood clot. The inflatable member at the end of the catheter device is subsequently guided along the guide wire in an over-the-wire fashion through the plaque occlusion. Therefore, the inflatable member and a tip of the catheter are distal to the blood clot.

There may be performed a step of localization of the inflatable member, for instance if detectable markers are provided in register with the inflatable member on the catheter device. Fluoroscopic imagery may be used to locate the inflatable member relative to the thrombus in the treated artery.

According to 56, the inflatable member is inflated distal of the blood clot. In doing so, microparticles of the thrombus are prevented from moving distally by the presence of the inflatable member blocking the artery distal of the occlusion. Hence, the inflatable member provides distal protection from embolization.

According to 58, a pharmacologic agent is infused into the infarction zone beyond the occlusion and the inflated member, and therefore downstream of the blood clot. As the artery is blocked by the inflated member, the pharmacologic agent is absorbed locally.

The infusion of the pharmacologic agent may be performed prior to the inflating of the inflatable member.

According to 60, the blood clot is vacuumed out of the artery so as to open the artery. Any free microparticles are held in the artery upstream of the inflated member, and thus vacuumed as well.

Subsequently, the various steps for terminating the intervention are performed, including the removal of the catheter device. It is pointed out that the method 50 may be performed according to any suitable sequence.

The invention claimed is:

1. A method for treating an artery having sequentially a proximal portion, a thrombus portion in which a thrombus occludes the artery, and a distal portion, the method comprising:
    percutaneously positioning a catheter in the artery in the proximal portion of the artery, the catheter having an infusion tube;
    positioning a single inflatable member of the catheter in the proximal portion of the artery;
    passing a tip of the infusion tube through the thrombus;
    inflating the inflatable member in the proximal portion of the artery; and
    infusing at least one pharmacologic agent distally to the thrombus in the distal portion via the infusion tube while the thrombus occludes the artery.

2. The method according to claim 1, wherein inflating the inflatable member proximally to the thrombus is performed prior to infusing at least one pharmacologic agent distally to the thrombus.

3. The method according to claim 1, wherein positioning the catheter further comprises positioning an aspiration tube of the catheter proximally to the thrombus.

4. The method according to claim 3, further comprising performing an aspiration via the aspiration tube while deflating the inflatable member to aspire the thrombus.

5. The method according to claim 4, wherein performing the aspiration is initiated after deflating the inflatable member is initiated.

6. The method according to claim 1, to wherein positioning the catheter and passing of the tip are done by moving the catheter over a guide wire.

7. The method according to claim 6, wherein moving the catheter over the guide wire comprises moving the catheter and the infusion tube simultaneously.

8. The method according to claim 7, wherein moving the catheter over the guide wire comprises moving the catheter and the infusion tube simultaneously by the infusion tube sliding on the guide wire.

9. The method according to claim 1, wherein infusing the at least one pharmacologic agent distally to the thrombus in the distal portion via the infusion tube includes infusing the at least one pharmacologic agent from an axially-facing distal opening from the infusion tube.

10. The method according to claim 1, wherein infusing the at least one pharmacologic agent distally to the thrombus in the distal portion via the infusion tube includes infusing the at least one pharmacologic agent in a proximal-to-distal axial direction of the artery.

11. A method for treating an artery having sequentially a proximal portion, a thrombus portion in which a thrombus occludes the artery, and a distal portion, the method comprising:
    percutaneously positioning a catheter with an infusion tube in the artery proximally to the thrombus and with a single inflatable member, the single inflatable member being positioned proximally to the thrombus in the proximal portion of the artery;
    passing a tip of the infusion tube through the thrombus;
    inflating the inflatable member in the proximal portion of the artery; and
    infusing at least one pharmacologic agent distally to the thrombus in the distal portion via the infusion tube.

* * * * *